United States Patent [19]

Freeman

[11] 3,999,540
[45] Dec. 28, 1976

[54] FASTENER MEANS FOR A LEG BRACE TO CONNECT TO A SHOE

[76] Inventor: Gordon J. Freeman, 9900 SW. 130 St., Miami, Fla. 33176

[22] Filed: Jan. 8, 1976

[21] Appl. No.: 647,551

[52] U.S. Cl. .......................................... 128/80 R
[51] Int. Cl.² .......................................... A61F 3/00
[58] Field of Search ............ 128/80 R, 80 F, 80 E, 128/80 A, 80 B, 88, 87 R, 83

[56] References Cited
UNITED STATES PATENTS

| | | | |
|---|---|---|---|
| 1,792,155 | 2/1931 | Fisher | 128/80 E |
| 2,267,848 | 12/1941 | Taylor | 128/80 R X |
| 2,439,100 | 4/1948 | Richards | 128/80 E |
| 3,844,279 | 10/1974 | Konvalin | 128/80 F |

Primary Examiner—John D. Yasko

[57] ABSTRACT

A fastener means for connecting a leg brace with a pair of distal ends having tongues to fit within a socket of a reinforced zone of a shoe, which consists of a first and a second forwardly extending finger each of which are adapted to overlie one another beneath the sole of a shoe and just forwardly of the heel and to be fastened together while the other ends are connected to the lower distal ends of the brace, so that the distal ends of the brace do not move outwardly from the sockets in the T-shaped member within the shoe.

5 Claims, 4 Drawing Figures

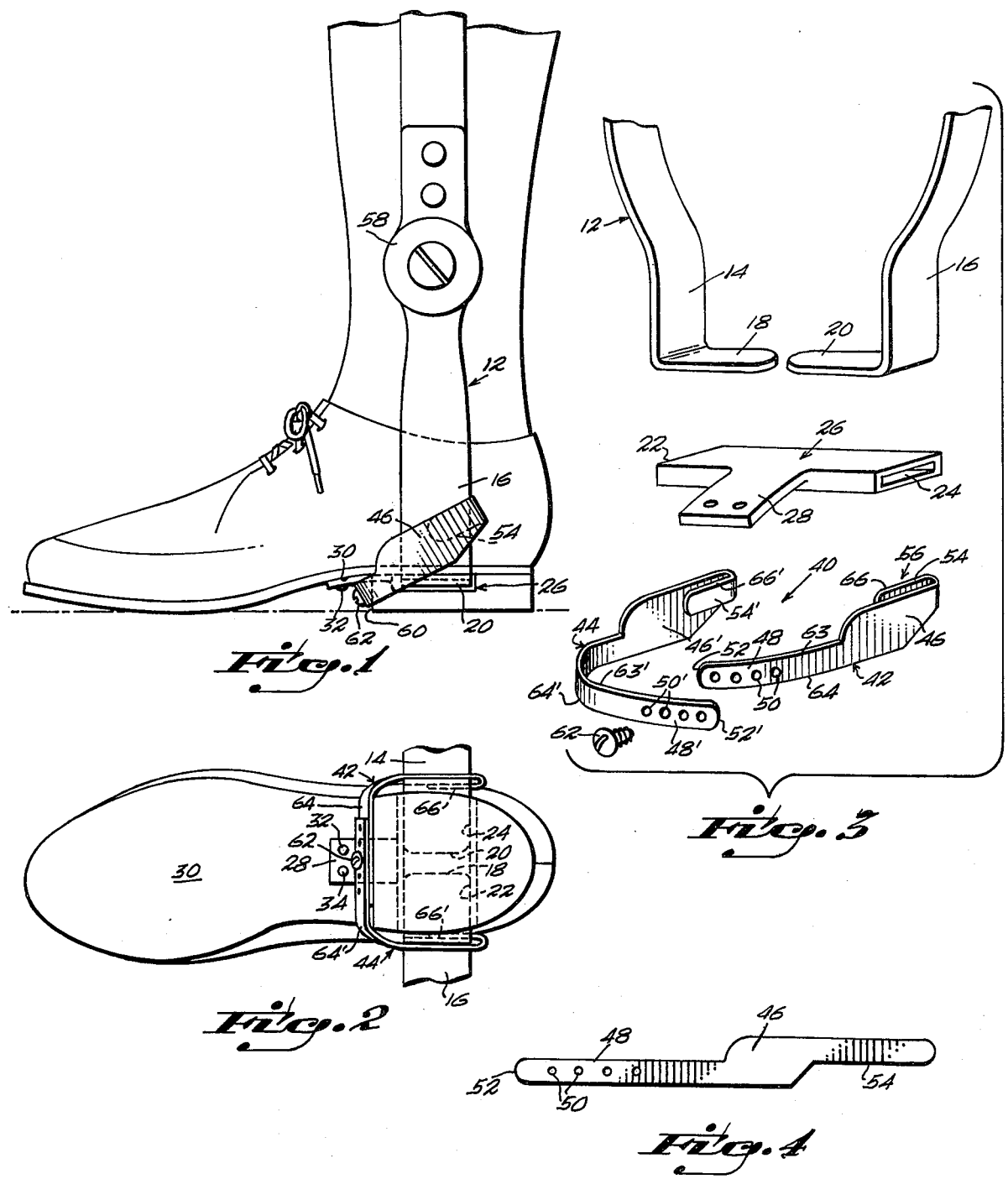

FASTENER MEANS FOR A LEG BRACE TO CONNECT TO A SHOE

FIELD OF THE INVENTION

This invention relates to leg braces and, more particularly, to an improvement in securing leg braces to a shoe so that loss of support does not result.

BACKGROUND OF THE INVENTION

In the past leg braces conventionally are provided with lower distal ends with inturned confronting portions which are received within a reinforced portion of a shoe and spring-urged to remain within slots. The problem has been that the distal ends sometimes slip out of the slots with an attendant loss of support.

In the past, various devices have been utilized to hold the internal or confronting portions of the leg braces in the reinforced slot zones of the heels of shoes. These means have included screws which extend vertically through the sole and engage the T-shaped members; however, when such screws are used, the shoe is permanently fastened to the leg brace, which is undesirable because a person wearing a leg brace often times desires to remove his shoe. Other solutions have been to utilize ties about the ankle zone which hold the lower distal ends of the brace together. This invention is of an improved fastener means for holding the lower ends of a leg brace together.

This invention has as an object the provision of a fastener means which includes a body arranged on the lower distal end of the leg brace of a wearer's leg and which engages, either by hooked-up relationship therewith, or by other fastener means, and which include finger means which are fastened together beneath the shoe in the crotch defined by the sole and the heel.

It is a general object of this invention to provide an improved fastener means for securing the lower distal ends of leg braces to shoes which can be easily and quickly released yet when in engagement provides a secure connection with the shoe.

Generally speaking the invention comprises an orthopedic brace lock means to connect to a shoe which is in two sections, each of which are of strip form spring steel, in the preferred embodiment, of about 8½ inches in length which are provided with a rearward hooked portion formed by bending the rearward portion upon itself for hooked-up engagement with the lower distal ends of a leg brace with a finger extending about the heel of the shoe and nestled in the crotch between the front face of the heel and the lower face of the sole, with the fastening of the fingers being by a screw which is threaded and in mating engagement with a pair of aligned holes in the fingers, so that it may be easily removed and with the device, thus, being adapted for connection to any conventional leg brace and shoe.

DESCRIPTION OF THE DRAWINGS

FIG. 1 is a partial side elevational view of a leg brace installed on a shoe;

FIG. 2 is a bottom plan view of the leg brace and fastener means of the instant invention;

FIG. 3 is a view in exploded form illustrating respectively the leg brace, the T-shaped member for inclusion in the heel of a shoe and a fastener means for connecting the lower distal ends of the leg brace in the slots of the T-shaped member; and FIG. 4 is a side elevation view of a fastener means of the type shown in FIG. 3.

DESCRIPTION OF PREFERRED EMBODIMENT

The numeral 12 indicates the lower distal end of a leg brace. It includes a left and right spaced distal end 14 and 16, see FIG. 3, each of which includes a tongue 18 and 20 in confronting relation for spring urged receipt in sockets 22 and 24 of a generally T-shaped member 26 which is conventionally built into the heel of a shoe, see FIGS. 1 and 2, with the forwardly and downwardly extending stem 28 being secured to the underside 30, that is the sole of the shoe as at 32 and 34. This structure is conventional; however, it gives rise to the problem that, from time to time, in use one or the other, or both, of the confronting tongues 18 and 20 slip out of their respective slots in the T-shaped member in which they are captivated or connected to the shoe heel with an attendant loss of support and danger from injury by falling.

The present invention provides fastening means to secure the tongues of the lower distal brace ends to the T-shaped member, as will now be described. The fastener means generally designated by the numeral 40 in FIG. 3 includes a first and a second member 42 and 44, which are preferably of spring steel in strip form. Each comprises a generally Z-shaped body, see FIG. 4, where it is shown as a mirror image of a "Z." Each includes (a) a central portion 46, (b) an elongate forwardly projecting finger 48, which extends from the lower front zone of the central portion and is provided with a plurality of longitudinally spaced holes, such as 50, therealong, extending proximally from the tip 52 toward the body's central portion, and (c) a rearwardly extending relatively short finger 54 which projects from the upper rear zone of the central portion and which is adapted to be bent back into spaced parallel relation to the upper zone of the central body portion defining a hook 56, as shown in FIG. 3, with the bight of the hook being adapted for hooked-up engagement with one of the distal ends of the leg brace.

In use, as shown in FIGS. 1 and 2, the tongues on the distal ends of the leg brace, which are rotatable on lateral pivot means 58, are inserted into their respective slots of the T-shaped member in the shoe heel. Thereafter, the hooked-up rearwardly extending fingers 54 and 54' are positioned in hooked-up engagement with the lower end zones of the brace and their respective forwardly extending fingers are bowed forwardly and inwardly into overlapped relation about the sides and front face 60 of the heel and beneath the stem of the T-shaped member where they are fastened or tied together by the screw 62 which is threaded for mating engagement in an aligned pair of holes 50.

For brevity of this description, corresponding parts of the fastener means of the pair of strip form strip steel Z-shaped members are designated by conventional numerals and corresponding numerals bearing a prime designation.

Thus, the relatively sharp upper and lower edges 63 and 64 and 63' and 64' of the forwardly extending fingers engage the stem of the T-shaped member extending forwardly from the heel underneath the sole and grip the juncture of the side and front face of the heel and are completely nested in the crotch beneath the shoe which is formed between the heel and the sole, while the upper edges 66 and 66' of the hooked rearwardly projecting fingers engage the respective distal ends of the leg brace. The fastener means are adapted to be permanently included as a part of the leg brace in which event the rearward fingers or the body portion may be welded or otherwise suitably fastened to the distal ends of the leg braces with the forwardly extending fingers being adapted for connection beneath the sole of the shoe; or, as shown in the preferred embodiment, the fastener means may be adapted to be separately attached by hooked-up engagement with the leg brace distal ends.

What is claimed is:

1. A leg brace having a pair of spaced downwardly extending pivotal distal ends and a tongue extending from each distal end in confronting relation with one another and received in a T-shaped socket defining means for connecting to a shoe and a pair of fastening means in strip form having a forwardly extending finger on each of said distal ends with a distal inturned portion sized to nest beneath the sole of a shoe and in the crotch formed by the heel and sole of the shoe and means to releasably tie the fingers together in the crotch to limit movement of separation of the distal ends of the brace and rearwardly extending fingers on each fastening means to secure to the distal ends of said leg brace.

2. The device as set forth in claim 1 wherein the fingers are of elongate spring steel in strip form.

3. The device as set forth in claim 2 wherein the means to tie comprise a plurality of holes of common size in each of the fingers and a headed screw sized for threaded mating engagement of a pair of aligned holes when the fingers are in overlapped relation in the crotch of the shoe.

4. The device as set forth in claim 1 wherein the fingers include a proximal central body portion and means to secure each of the body portions to one of the distal ends.

5. The device as set forth in claim 4 wherein the means comprise rearwardly extending forwardly opening hook means sized for hooked-up engagement with the distal ends of the leg brace.

* * * * *